(12) United States Patent
Haibach

(10) Patent No.: US 9,333,313 B2
(45) Date of Patent: May 10, 2016

(54) PATIENT INTERFACE DEVICE WITH DYNAMIC MASK ADJUSTMENT

(75) Inventor: Richard Thomas Haibach, Verona, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 632 days.

(21) Appl. No.: 13/583,085

(22) PCT Filed: Feb. 24, 2011

(86) PCT No.: PCT/IB2011/050781
§ 371 (c)(1),
(2), (4) Date: Sep. 6, 2012

(87) PCT Pub. No.: WO2011/110968
PCT Pub. Date: Sep. 15, 2011

(65) Prior Publication Data
US 2013/0000646 A1    Jan. 3, 2013

Related U.S. Application Data

(60) Provisional application No. 61/313,141, filed on Mar. 12, 2010.

(51) Int. Cl.
*A61M 16/00* (2006.01)
*A61M 16/06* (2006.01)
*A61M 16/08* (2006.01)

(52) U.S. Cl.
CPC ............ *A61M 16/06* (2013.01); *A61M 16/0638* (2014.02); *A61M 16/0683* (2013.01); *A61M 16/0816* (2013.01)

(58) Field of Classification Search
CPC ............ A61M 16/06; A61M 16/0633; A61M 16/0638; A61M 16/0644; A61M 16/065; A61M 16/0655; A61M 16/0605
USPC .............. 128/106.28, 207.11, 207.14, 207.17
See application file for complete search history.

(56) References Cited

U.S. PATENT DOCUMENTS

| | | | |
|---|---|---|---|
| 7,069,932 B2* | 7/2006 | Eaton et al. ............... | 128/206.24 |
| 8,596,273 B2* | 12/2013 | Burz et al. ............... | 128/206.21 |
| 2006/0260614 A1* | 11/2006 | Biener et al. ............. | 128/206.21 |
| 2007/0277827 A1 | 12/2007 | Bordewick | |
| 2008/0314388 A1* | 12/2008 | Brambilla et al. ....... | 128/205.25 |
| 2008/0314390 A1* | 12/2008 | Kwok et al. ............. | 128/207.11 |
| 2011/0259337 A1* | 10/2011 | Hitchcock et al. ....... | 128/207.11 |

FOREIGN PATENT DOCUMENTS

| | | |
|---|---|---|
| CN | 101102806 A | 1/2008 |
| CN | 201275352 Y | 7/2009 |
| EP | 1475118 A1 | 11/2004 |
| JP | 2003175106 A | 6/2003 |
| WO | WO2005068002 A1 | 7/2005 |

* cited by examiner

*Primary Examiner* — Valerie L Skorupa
*Assistant Examiner* — Douglas Sul
(74) *Attorney, Agent, or Firm* — Michael W. Haas

(57) ABSTRACT

A patient interface device (10, 10', 62, 62', 102, 152, 162, 172) is provided that includes a patient sealing assembly (12, 64, 104), such as a mask having a rigid shell and a cushion coupled to the rigid shell, a forehead support (26, 72, 118) coupled to the patient sealing assembly, and a hinge assembly (40, 40', 84, 84', 124, 154, 164, 174) provided between a top portion of the patient sealing assembly and the forehead support.

15 Claims, 12 Drawing Sheets

PATIENT INTERFACE DEVICE WITH DYNAMIC MASK ADJUSTMENT

CROSS-REFERENCE TO RELATED APPLICATIONS

This patent application claims the priority benefit under 35 U.S.C. §371 of international patent application no. PCT/IB2011/050781, filed Feb. 24, 2011, which claims the priority benefit under 35 U.S.C. §119(e) of U.S. Provisional Application No. 61/313,141 filed on Mar. 12, 2010, the contents of which are herein incorporated by reference.

BACKGROUND OF THE INVENTION

1. Field of the Disclosure

The present invention relates to patient interface devices for communicating a flow of gas with an airway of a user, and, in particular, to a patient interface device including a mechanism for dynamically adjusting a mask of the patient interface device.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. The patient interface device interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Because such patient interface devices are typically worn for an extended period of time, it is important for the headgear to maintain the mask component of the device in a tight enough seal against the patient's face without discomfort. One area where fit and comfort is often a concern is the bridge of the patient's nose, as most patient interface devices will apply a pressure to this area. If this pressure is not able to be managed effectively, either or both of a poor fit or patient discomfort will result, thereby limiting the effectiveness of the device.

SUMMARY OF THE INVENTION

In one embodiment, a patient interface device is provided that includes a patient sealing assembly, such as, without limitation, a mask having a rigid shell, and a cushion coupled to the rigid patient sealing assembly, a forehead support coupled to the patient sealing assembly, and a hinge assembly provided between a top portion of the patient sealing assembly and the forehead support. In one particular embodiment, the hinge assembly includes a support arm having a distal end directly or indirectly coupled to the forehead support, wherein the hinge assembly is structured to move in manner wherein the support arm moves toward a sealing plane defined by a sealing surface of the patient sealing assembly. The patient interface device may include a strap frame structured to be coupled to a plurality of upper headgear straps, wherein the strap frame is located between the distal end of the support arm and the forehead support, and wherein the hinge assembly is structured to move in response to strapping forces being applied by the upper headgear straps when the patient interface device is donned by a patient.

The patient interface device may alternatively include a hinge assembly that includes second and third support arms extending upwardly from the shell, wherein the support arm is moveably received and held between the second and third support arms. The second and third support arms may each include an extension member having a distal end structured to be coupled to a respective upper headgear strap of a headgear component, wherein the hinge assembly is structured to move in response to strapping forces being applied by the upper headgear straps when the patient interface device is donned by a patient.

In another embodiment, a pressure support system is provided that includes a pressure generating device structured to produce a flow of breathing gas, and a patient interface device operatively coupled to the pressure generating system and structured to deliver the flow of breathing gas to an airway of a patient, wherein the patient interface device includes a patient sealing assembly, a forehead support coupled to the patient sealing assembly, and a hinge assembly provided between a top portion of the patient sealing assembly and the forehead support.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
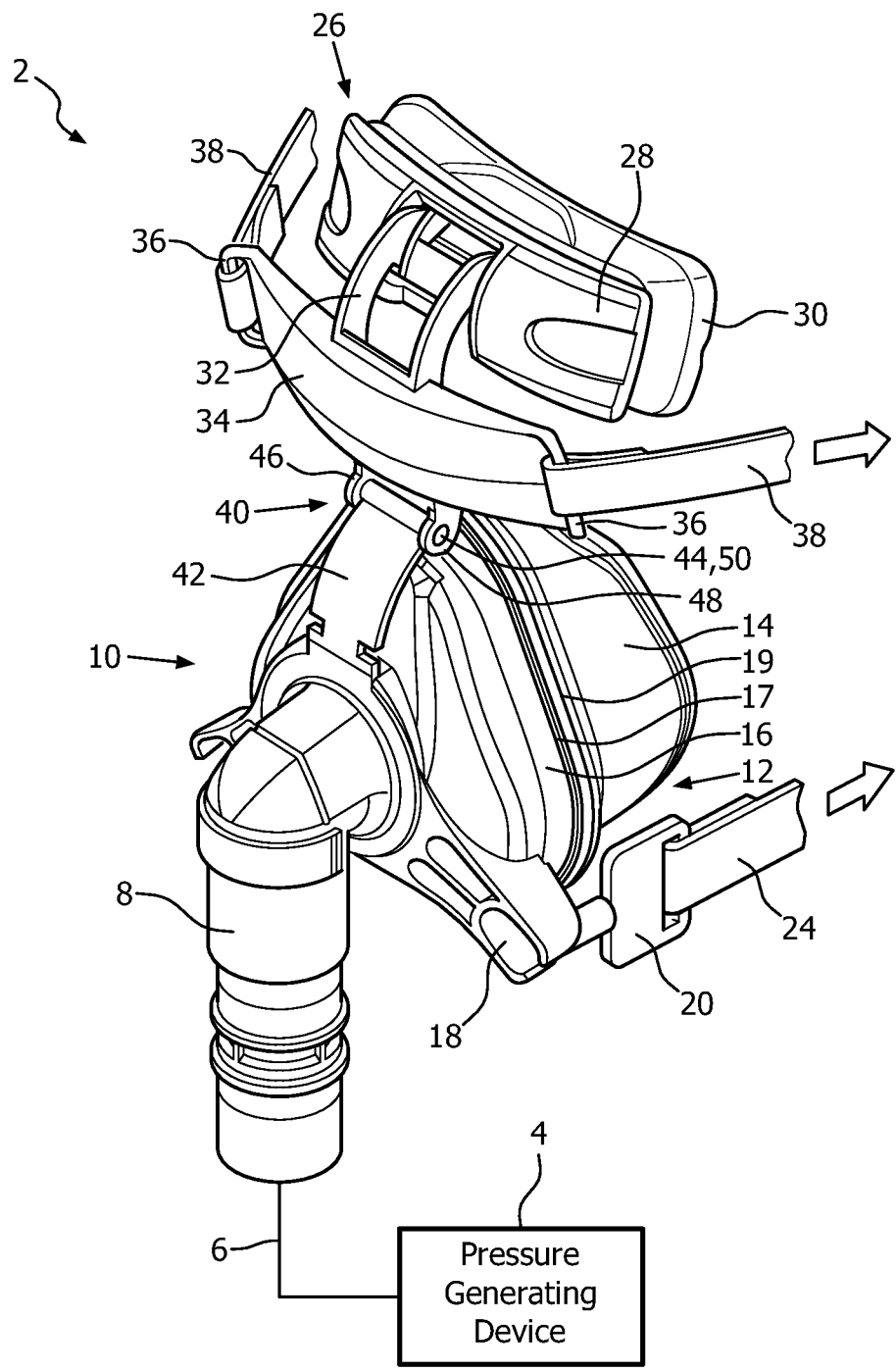
FIGS. 1-3 are isometric, front, and side schematic diagrams of a system adapted to provide a regimen of respiratory therapy to a patient according to one embodiment of the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 2:
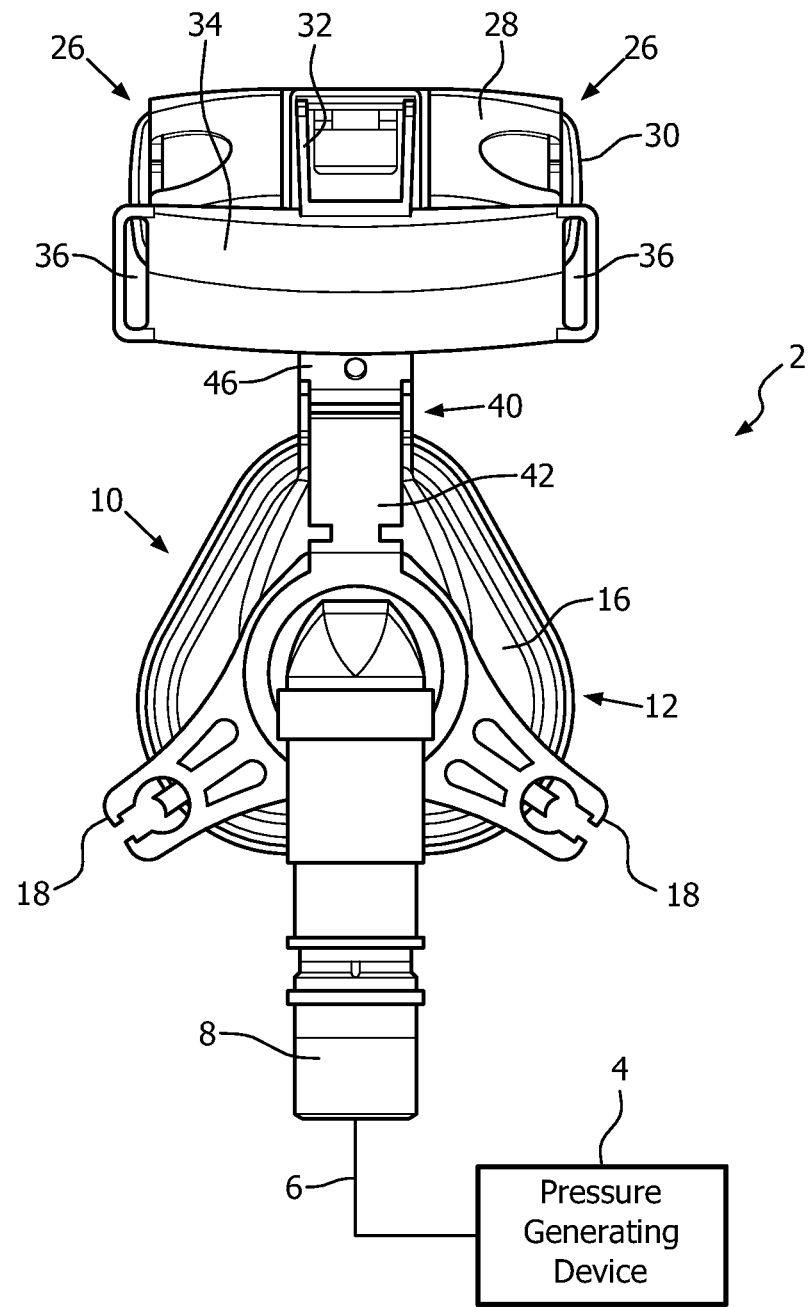
Figure 3:
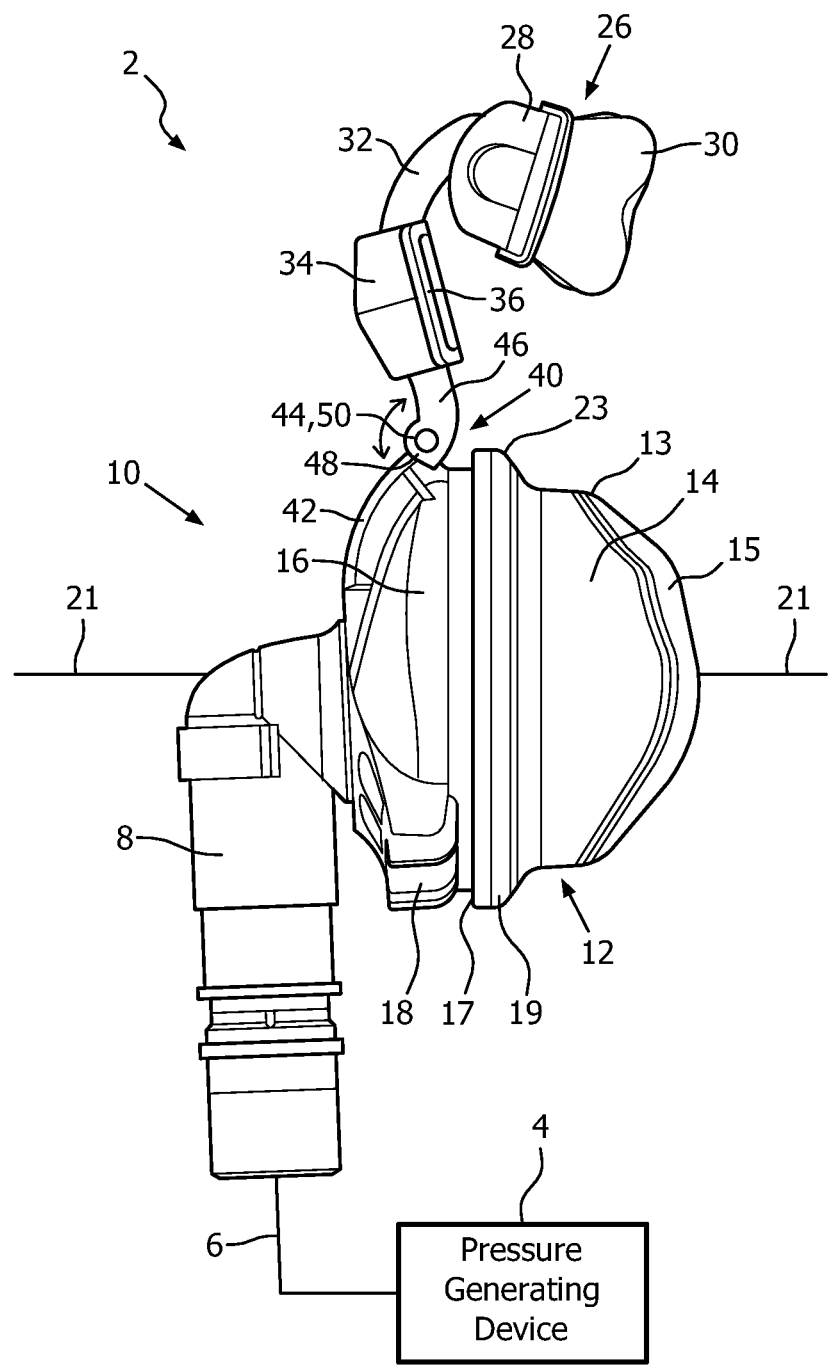

Pressure support system 2 adapted to provide a regimen of respiratory therapy to a patient according to one embodiment is generally shown in FIGS. 1-3. System 2 includes a pressure generating device 4, a delivery conduit 6 coupled to elbow connector 8, and a patient interface device 10. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 10 through elbow connector 8. Delivery conduit 6, elbow connector 8 and patient interface device 10 are often collectively referred to as a patient circuit.

Patient interface device 10 includes a patient sealing assembly 12, which in the illustrated embodiment is a mask, and, in particular, a nasal mask. However, any type of patient sealing assembly, such as a nasal/oral mask, a nasal cushion, nasal prongs or cannula, or a full face mask, which facilitates the delivery of the flow of gas to the airway of a patient, may be substituted for mask while remaining within the scope of the present invention. Mask 12 includes a cushion 14 coupled to a rigid shell 16. An opening in shell 16, to which an elbow connector 8 is coupled, allows the flow of breathing gas from pressure generating device 4 to be communicated to an interior space defined by shell 16 and cushion 14, and then to the airway of a patient.

In addition, cushion 14 includes a sealing surface 15 that is structured to engage the face of a patient when patient interface device 10 is donned by the patient. At least a portion of sealing surface 15 generally defines a sealing plane that is tangential to sealing surface 15 and generally parallel to a surface 17 of cushion 14 defined by an outer edge 19 of the cushion that engages shell 16. It will be appreciated that the sealing plane will not be an entirely flat plane as the human face is not flat. As seen in FIG. 3, a centerline 21 that passes though cushion 14 along the longitudinal axis of the cushion an is generally normal to this sealing plane.

Shell 16 includes first and second headgear connection elements 18 in the form of slots or sockets, each structured to receive and hold a catch of a clip element 20. In the exemplary embodiment, the slots and clip elements 20 are structured in the form of a ball and socket configuration. Each clip element 20 also includes loop 22 for receiving a respective lower headgear strap 24 of a headgear component used to secure patient interface device 10 to the head of the patient.

Patient interface device 10 further includes a forehead support 26 that, in the illustrated embodiment, includes a support frame 28 coupled to a forehead cushion 30. Forehead support 26 is structured to provide support for patient interface device 10 by engaging the forehead of the patient. Support frame 28 is moveably (in the illustrated embodiment pivotably) coupled to upper arm 32, which, in turn, is coupled to an upper strap frame 34. Upper strap frame 34 includes loops 36 provided at opposite ends thereof. Each loop 36 is structured to receive a respective upper headgear strap 38 of the headgear component. As is known, lower headgear straps 24 and upper headgear straps 38 enable the headgear component of which they are a part to secure patient interface device 10 to the patient's head.

As seen in FIGS. 1-3, upper strap frame 34 is positioned a distance below forehead support 26. The significance of this relative positioning is described elsewhere herein.

Figure 4:
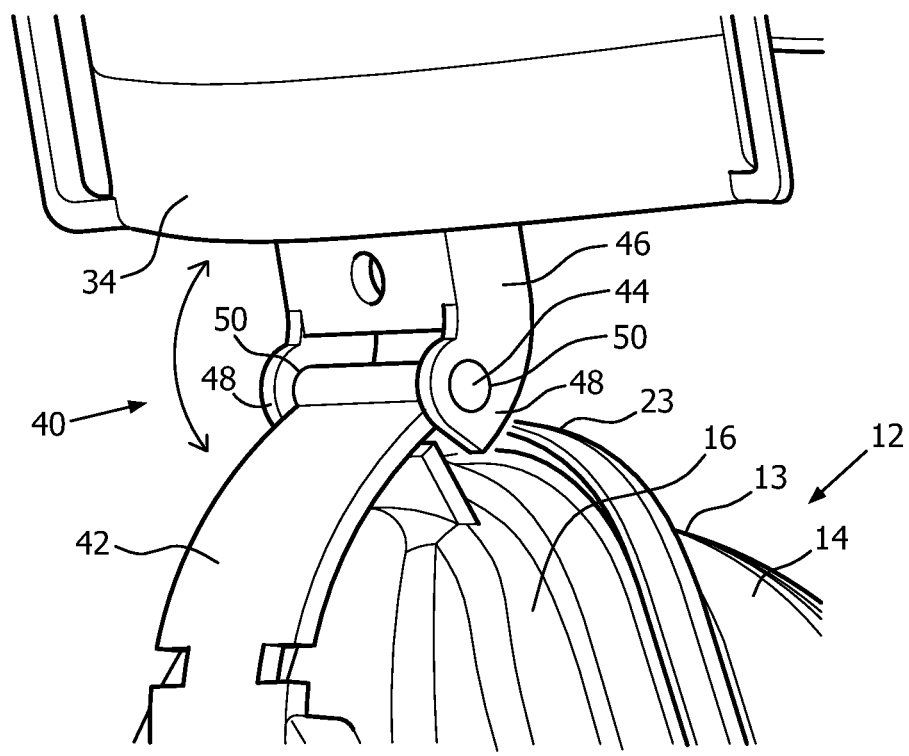
FIG. 4 is magnified view of a hinge assembly forming a part of the exemplary patient interface device embodiment employed in the system embodiment of FIGS. 1-3.

Patient interface device 10 further includes a hinge assembly 40 that is provided between shell 16 and the bottom of upper strap frame 34. A magnified view of hinge assembly 40 is shown in FIG. 4. Hinge assembly 40 includes a lower support arm 42 that is coupled to shell 16. The top end of lower support arm 42 is provided with pins 44 on opposite sides thereof. Hinge assembly 40 further includes an upper support arm 46. The top end of upper support arm 46 is coupled to the bottom of upper strap frame 34, and the bottom end of upper support arm 46 is provided with extensions 48 each having an orifice 50 provided therein. Each pin 44 is rotatably received within a respective orifice 50 to create a hinge which allows upper support arm 46 to move (e.g., pivot) relative to lower support arm 42 as shown by the arrows in FIGS. 3 and 4.

Patient interface device 10 as just described provides a mechanism for selectively (and finely) adjusting the force applied to the bridge of the nose of a patient by apex portion 13 of cushion 14 of mask 12 by varying the force applied by upper headgear straps 38. The ability to provide subtle adjustments helps to minimize leaks and provide comfort to the patient. More specifically, as upper headgear straps 38 are tightened, the force applied by upper headgear straps 38 causes upper arm 32, upper strap frame 34 and upper support arm 46 to move (e.g., pivot) toward the sealing plane described above. During such movement, forehead support 26 is a fixed point of contact with the user. When patient interface device 10 is worn by a patient, such movement will cause upper arm 32, upper strap frame 34, upper support arm 46 to move toward the face of the patient (with forehead support 26 being a fixed point of contact). As the upper arm 32, upper strap frame 34 and upper support arm 46 move in this manner, the hinge of hinge assembly 40 is allowed to rotate and close. As the hinge of hinge assembly 40 actuates by opening and closing, the nose bride force applied by an apex portion 13 of cushion 14 of mask 12 is varied and controlled, because top portion 23 of mask 16 will be caused to move relative to the patient's face (toward or away from the sealing plane described above). The bottom portion of mask 12 is secured in place by the force applied by lower headgear straps 24. Thus, this configuration of patient interface assembly provides the user with the ability to control the force applied on the nose bridge area, for example, in the case of a nasal mask by lengthening or shorting the straps attached to frame 34.

Figure 5:
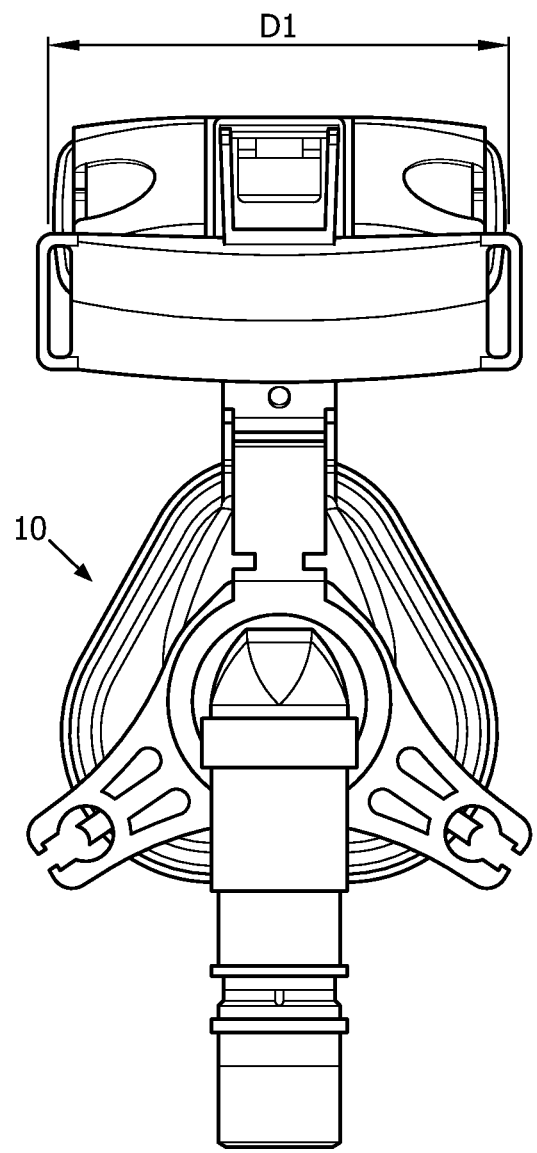
FIGS. 5 and 6 are front and side views, respectively, of the exemplary patient interface device embodiment employed in the system embodiment of FIGS. 1-3 showing certain relevant dimensions thereof.
Figure 6:
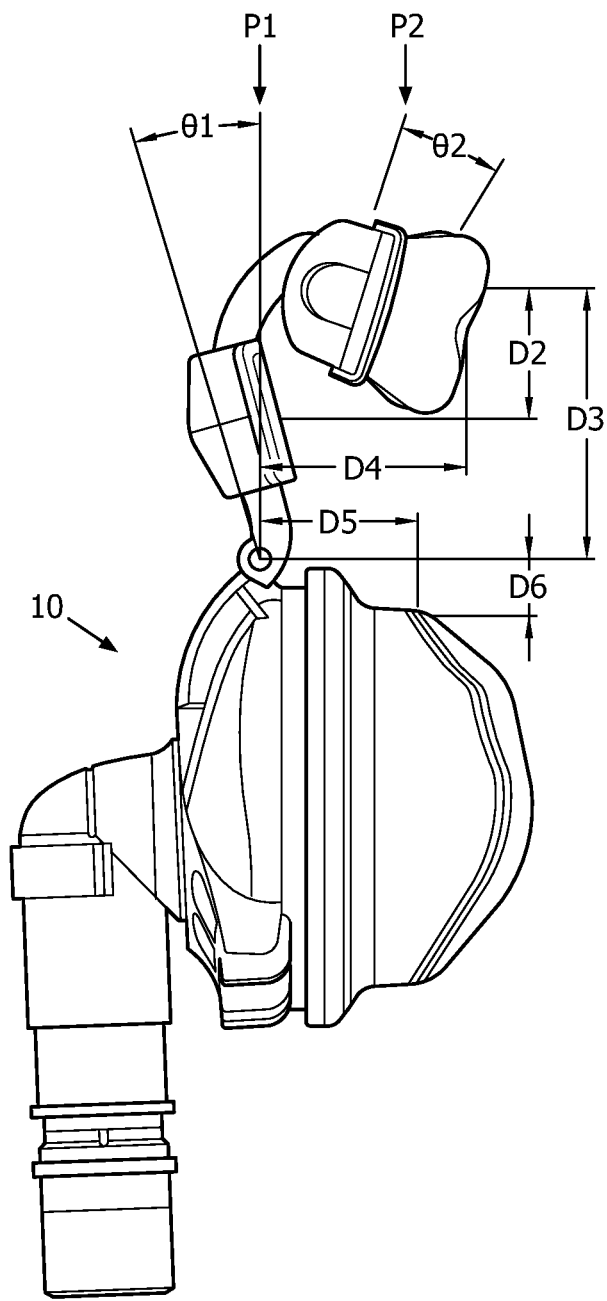

In one particular, non-limiting exemplary embodiment, patient interface device 10 includes the dimensions D1-D6 and θ1 and θ2 as shown in FIGS. 5 and 6, wherein D1 is approximately 50 mm, D2 is approximately 25 mm, D3 is approximately 50 mm, D4 is approximately 40 mm, D5 is approximately 25 mm, D6 is approximately 8 mm, θ1 (allowable tilt) is approximately 20 degrees or more, θ2 is approximately 25 degrees, and P1 and P2 refer to positions in the relaxed state. As will be appreciated, the particulars of the dimensions shown in FIGS. 5 and 6 (as they may be varied those set forth above) determine how the magnitude of the nose bridge force changes relative to and in response to the magnitude of the force applied by top headgear straps 38.

Figure 7:
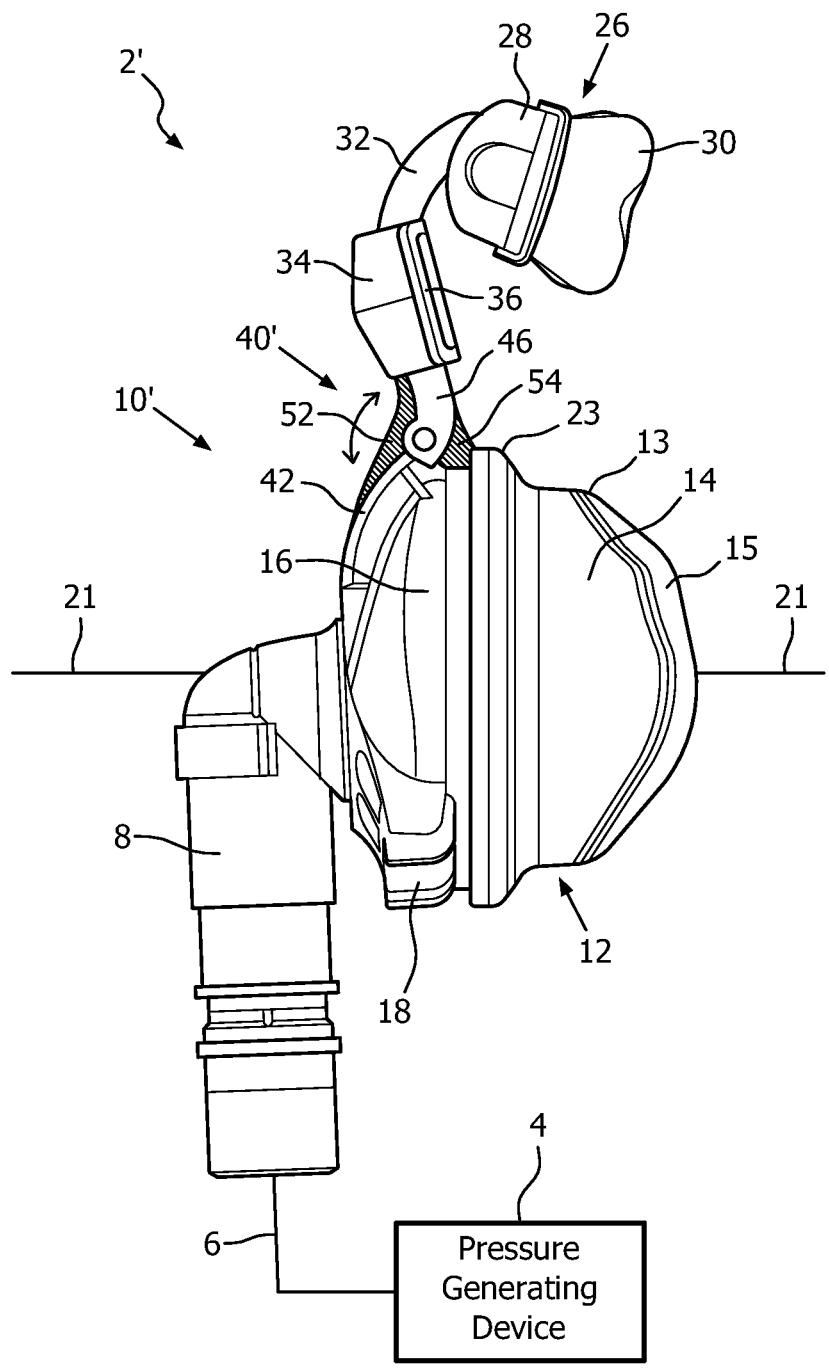
FIG. 7 is a side view of a system for providing a regimen of respiratory therapy to a patient according to an alternative embodiment that employs an alternative patient interface device.

FIG. 7 is a side view of system 2' for providing a regimen of respiratory therapy to a patient according to an alternative embodiment. System 2' differs from system 2 in that it includes an alternative embodiment of a patient interface device, namely patient interface device 10'. As seen in FIG. 7, patient interface device 10' includes all of the components of patient interface device 10 described elsewhere herein, and like components are labeled with like reference numerals.

Figure 8:
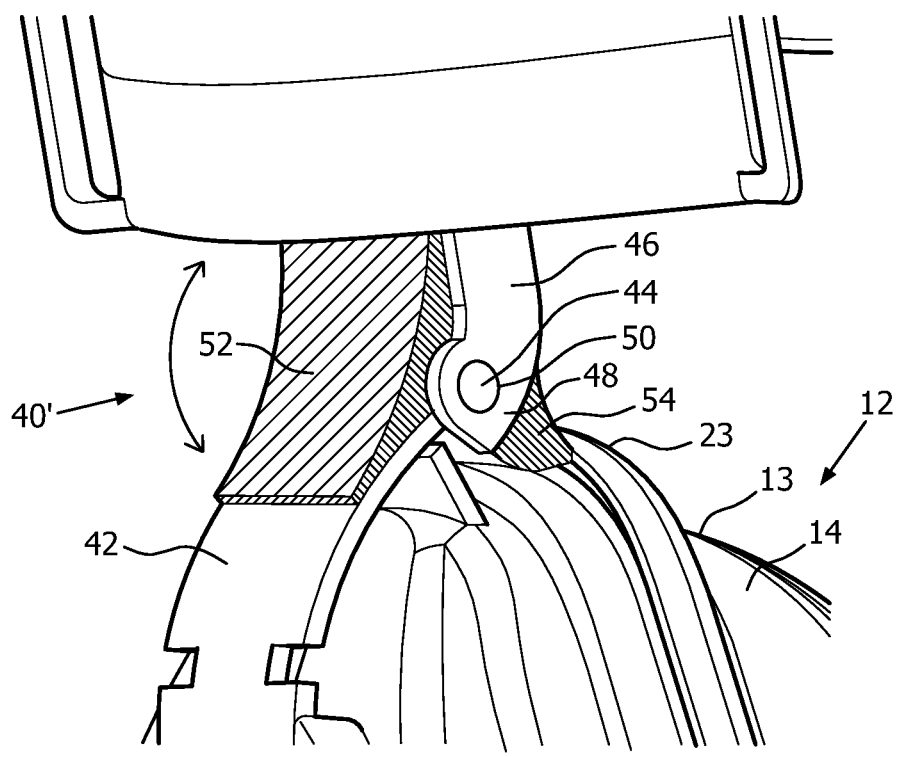
FIG. 8 is magnified view of an alternative hinge assembly forming a part of the patient interface device embodiment employed in the system embodiment of FIG. 7.

Patient interface device 10' further includes an alternative hinge assembly 40', a magnified view of which is shown in FIG. 8, that includes an elastomer member 52 provided on a front side of at least part of each of lower support arm 42 and an upper support arm 46, and an elastomer member 54 provided between the rear side of upper support arm 46 and the top of shell 16. Elastomer members 52 and 54 function to stiffen the joint formed at hinge assembly 40', and act as a spring member that functions to automatically return hinge assembly 40', and thus patient interface device 10', to a pre-set initial position and configuration when forces tending to close hinge assembly 40' as described elsewhere herein are removed. Elastomer members 52 and 54 thus provide patient interface device 10' with a self aligning capability that ensures, absent appropriate forces, patient interface device 10' will be in a consistent, pre-set initial position and configuration (for example, as shown in FIG. 7).

The elastomer members 52 and 54 may be made of a material such as silicone, rubber, polychloroprene, or another suitable elastomer material, and may be overmolded on lower support arm 42, upper support arm 46 and shell 16 with a self bonding material, or, alternatively, may be mechanically bonded to lower support arm 42, upper support arm 46 and shell 16. In addition, elastomer members 52 and 54 may be separate, discrete members or may be formed as parts of a unitary structure.

Figure 9:
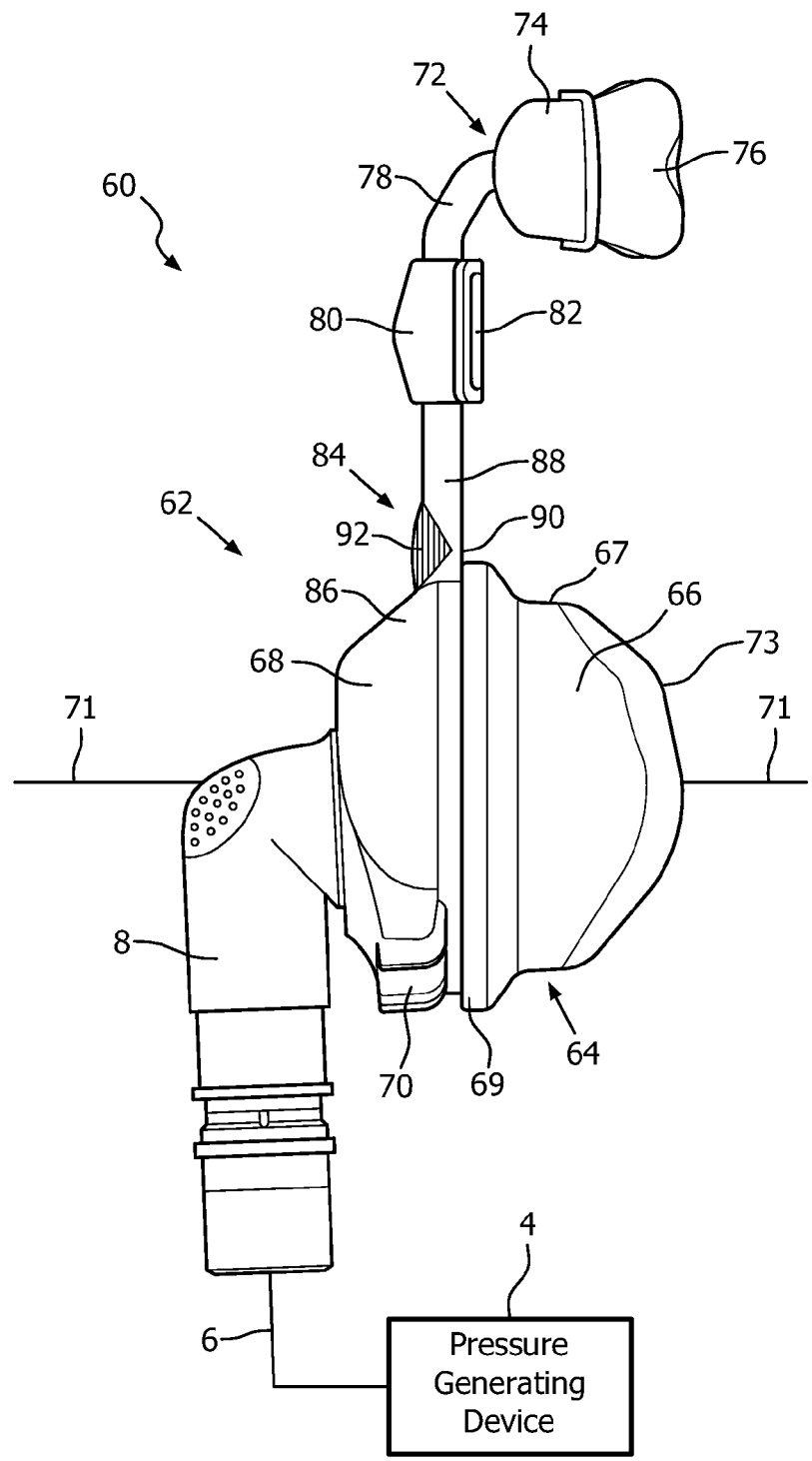
FIG. 9 is a side view of a system for providing a regimen of respiratory therapy to a patient according to a further alternative embodiment that employs a further alternative patient interface device.

FIG. 9 is a side schematic view of a system 60 adapted to provide a regimen of respiratory therapy to a patient according to an alternative exemplary embodiment of the invention. System 60 includes pressure generating device 4 and delivery conduit 6 coupled to elbow connector 8 as described elsewhere herein. In addition, system 60 includes a patient interface device 62 according to an alternative exemplary embodiment of the invention.

Patient interface device 62 includes a patient sealing assembly 64, which in the illustrated embodiment is mask in the form of a nasal mask. However, any type of patient sealing assembly, such as a nasal/oral mask, a nasal cushion or a full face mask, which facilitates the delivery of the flow of breathing gas to the airway of a patient, may be substituted for mask while remaining within the scope of the present invention. Mask 64 includes cushion 66 coupled to rigid shell 68. An opening in shell 68, to which elbow connector 8 is coupled, allows the flow of breathing gas from pressure generating device 4 to be communicated to an interior space defined by shell 68 and cushion 66, and then to the airway of a patient.

In addition, cushion 66 includes sealing surface 73 that is structured to engage the face of a patient when patient interface device 62 is donned by the patient. At least a portion of sealing surface 73 defines a sealing plane that is tangential to sealing surface 73 and parallel to a bottom surface of cushion 66 that engages shell 68. As seen in FIG. 9, centerline 71 that passes though cushion 66 along the longitudinal axis of cushion 66 is normal to the sealing plane.

Shell 68 includes first and second slots 70 each structured to receive and hold a catch of a clip element, such as clip element 20 shown in FIG. 1, that is coupled to a lower headgear strap, such as lower headgear strap 24 shown in FIG. 1, of a headgear component used to secure patient interface device 62 to the head of the patient.

Patient interface device 62 further includes a forehead support 72 that, in the illustrated embodiment, includes a support frame 74 coupled to a forehead cushion 76. Forehead support 72 is structured to provide additional support for patient interface device 62 by engaging the forehead of the patient. Support frame 74 is moveably (e.g., pivotably) coupled to upper arm 78, which in turn is coupled to upper strap frame 80. Upper strap frame 80 includes loops 82 provided at opposite ends thereof. Each loop 82 is structured to receive a respective upper headgear strap, such as upper headgear strap 38 shown in FIG. 1, of the headgear component.

As seen in FIG. 9, upper strap frame 80 is positioned a distance below forehead support 72. The significance of this relative positioning is described elsewhere herein.

Patient interface device 62 further includes hinge assembly 84 that is provided between top portion 86 of shell 68 and the bottom of upper strap frame 80. Hinge assembly 84 includes support arm 88, living hinge portion 90 and elastomer member 92. As seen in FIG. 9, the top end of support arm 88 is coupled to the bottom of upper strap frame 80, and the bottom end of support arm 88 is coupled to living hinge portion 90. In addition, elastomer member 92 is coupled to a front side of living hinge portion 90. Elastomer member 92 may be made of a material such as silicone, rubber, polychloroprene, or another suitable elastomer material, and may be overmolded on living hinge portion 90 with a self bonding material, or, alternatively, may be mechanically bonded to living hinge portion 90. Living hinge portion 90 and elastomer member 92 function to create a hinge which allows support arm 88 to move (e.g., pivot) relative to top portion 86 of shell 68 as described in greater detail below.

Patient interface device 62 as just described provides a mechanism for selectively (and finely) adjusting the force applied to the bridge of the nose of a patient by apex portion 67 of cushion 66 of mask 64 by varying the force applied by the upper headgear straps attached thereto. As noted elsewhere herein (in connection with patient interface device 10), the ability to provide subtle adjustments helps to minimize leaks and provide comfort to the patient. More specifically, as the upper headgear straps are tightened, the force applied by the upper headgear straps causes upper arm 78, upper strap frame 80 and support arm 88 to move (e.g., pivot) toward the sealing plane described above. In addition, when patient interface device 60 is worn by a patient, such movement will cause upper arm 78, upper strap frame 80 and support arm 88 to move toward the face of the patient (with forehead support 72 being a fixed point of contact). As the upper arm 78, upper strap frame 80 and support arm 88 move (e.g., pivot) in this manner, the hinge of hinge assembly 84 is allowed to rotate and close. As the hinge of hinge assembly 84 actuates by opening and closing, the nose bride force applied by apex portion 67 of cushion 66 of mask 64 is varied and controlled as the top of mask 64 will be caused to move relative to the patient's face (toward or away from the sealing plane described above). The bottom of mask 64 is secured in place by the force applied by the lower headgear straps attached thereto. In addition, alternative hinge assembly 84 provides for a self aligning capability as described elsewhere herein (FIGS. 7 and 8).

Figure 10:
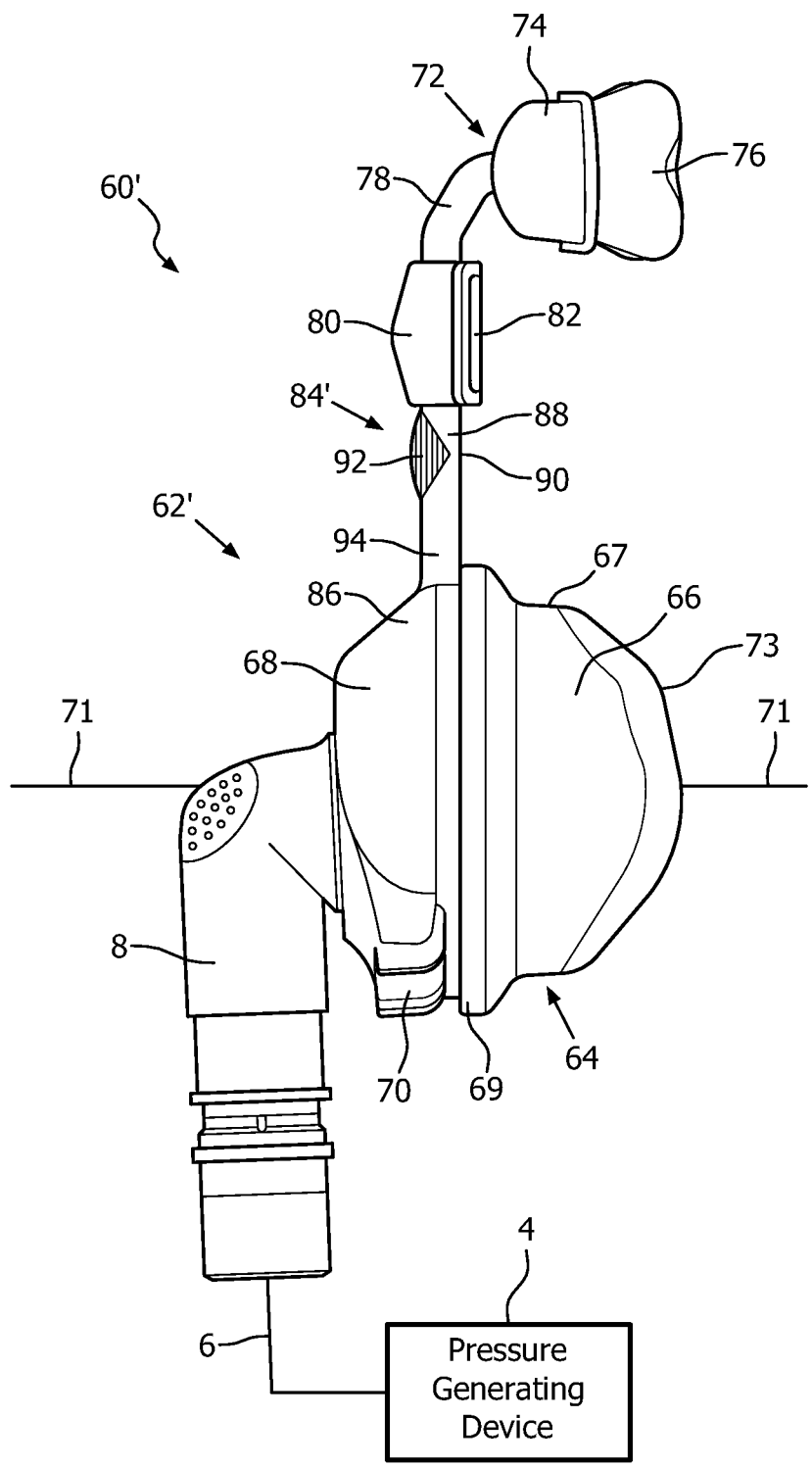
FIG. 10 is a side view of a system for providing a regimen of respiratory therapy to a patient according to still a further alternative embodiment that employs still a further alternative patient interface device.

FIG. 10 is a side schematic view of system 60' adapted to provide a regimen of respiratory therapy to a patient according to a further alternative exemplary embodiment of the invention. System 60' is similar to system 60, and like components are labeled with like reference numerals. System 60', however, includes an alternative patient interface device 62' having alternative hinge assembly 84'. Hinge assembly 84', like hinge assembly 84, includes support arm 88, living hinge portion 90 and elastomer member 92. As seen in FIG. 10, the top end of support arm 88 is coupled to the bottom of upper strap frame 80, and the bottom end of support arm 88 is coupled to living hinge portion 90. In addition, hinge assembly 84' includes second support arm 94, the top end of which is coupled to living hinge portion 90 and the bottom end of which is coupled to top portion 86 of shell 68.

In operation, as the upper headgear straps attached to upper strap frame 80 are tightened, the force applied by the upper headgear straps causes upper arm 78, upper strap frame 80 and support arm 88 to move (e.g., pivot) toward the sealing plane described elsewhere herein. In addition, when patient interface device 60 is worn by a patient, such movement will cause upper arm 78, upper strap frame 80 and support arm 88 to move toward the face of the patient (with forehead support 72 being a fixed point of contact). As the upper arm 78, upper strap frame 80 and support arm 88 move (e.g., pivot) in this manner, the hinge of hinge assembly 84' is allowed to rotate and close. As the hinge of hinge assembly 84' actuates by opening and closing, the nose bride force applied by apex portion 67 of cushion 66 of is varied and controlled as the top of mask 64 and second support arm 94 will be caused to move relative to the patient's face (toward or away from the sealing plane described above). The bottom of mask 64' is secured in place by the force applied by the lower headgear straps attached thereto. The respective lengths of support arm 88 and second support arm 94 can be varied to provide different responses to the forces applied by the upper headgear straps. In addition, alternative hinge assembly 84' provides for a self aligning capability as described elsewhere herein (FIGS. 7 and 8).

Figure 11:
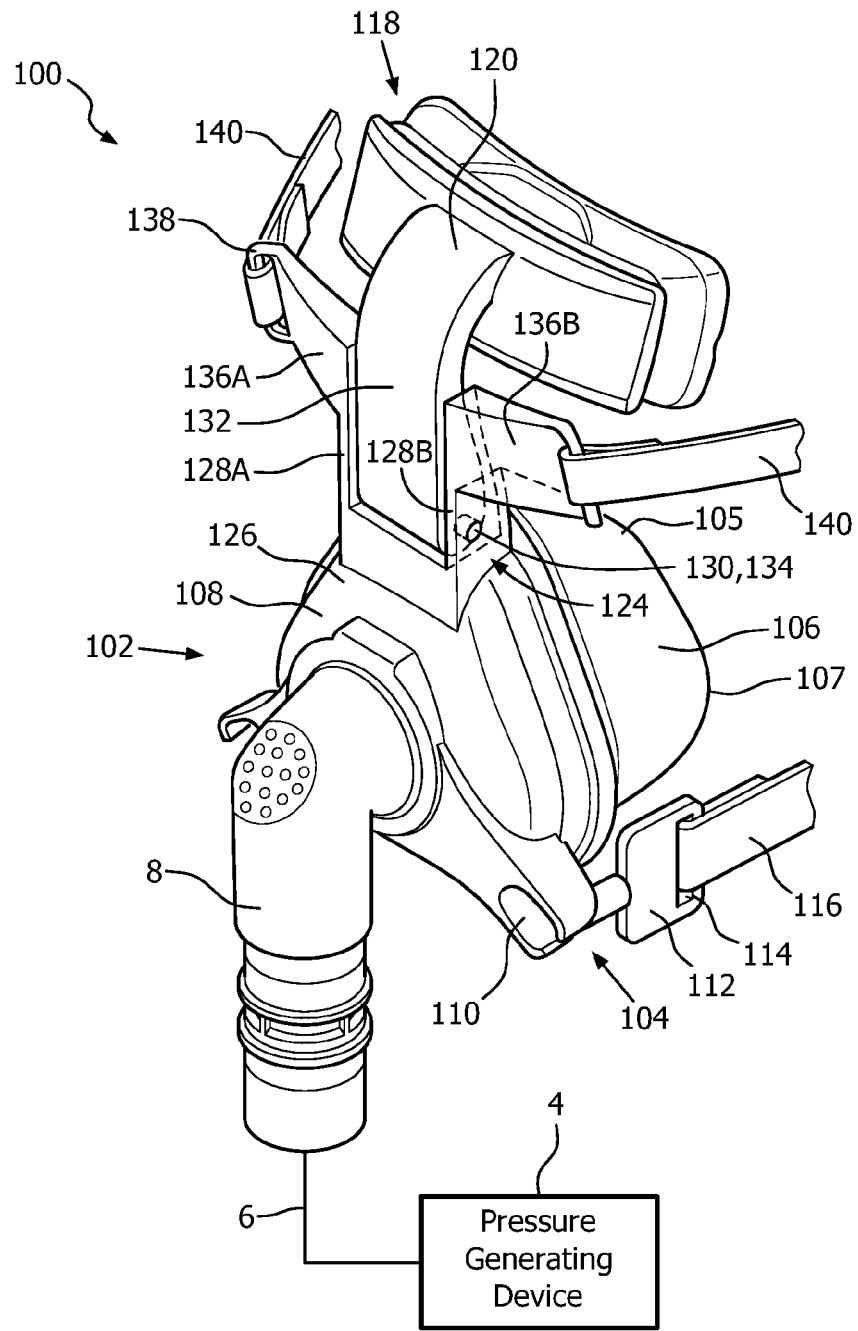
FIG. 11 is a side view of a system for providing a regimen of respiratory therapy to a patient according to yet another alternative embodiment that employs yet another further alternative patient interface device.

FIG. 11 is a side schematic view of a system 100 adapted to provide a regimen of respiratory therapy to a patient according to still a further alternative exemplary embodiment of the invention. System 100 includes pressure generating device 4 and delivery conduit 6 coupled to elbow connector 8 as described elsewhere herein. In addition, system 100 includes a patient interface device 102 according to an alternative exemplary embodiment of the invention.

Patient interface device 102 includes a patient sealing assembly 104, which in the illustrated embodiment is mask in the form of a nasal mask. However, any type of patient sealing assembly, such as a nasal/oral mask, a nasal cushion or a full face mask, which facilitates the delivery of the flow of breathing gas to the airway of a patient, may be substituted for mask while remaining within the scope of the present invention. Mask includes cushion 106 coupled to rigid shell 108. An opening in shell 108, to which elbow connector 8 is coupled, allows the flow of breathing gas from pressure generating device 4 to be communicated to an interior space defined by shell 108 and cushion 106, and then to the airway of a patient.

Shell 108 includes first and second slots 110 provided on opposite sides thereof, each structured to receive and hold a catch of clip element 112. In the illustrated embodiment, slots 110 and clip elements 112 are structured in the form of a ball and socket configuration. Each clip element 112 also includes loop 114 for receiving a respective lower headgear strap 116 of a headgear component used to secure patient interface device 102 to the head of the patient.

Patient interface device 102 further includes forehead support 118 that includes support frame 120 coupled to forehead cushion 122. Forehead support 118 is structured to provide additional support for patient interface device 102 by engaging the forehead of the patient.

Patient interface device 102 further includes hinge assembly 124 that is provided between top portion 126 of shell 108 and the bottom of support frame 120. Hinge assembly 40 includes lower support arms 128A and 128B that are each coupled to top portion 126 of shell 108. The top end of each lower support arm 128A, 128B is provided with an orifice 130. Hinge assembly 124 further includes upper support arm 132, wherein a top end of upper support arm 132 is coupled to support frame 120. The bottom end of upper support arm 132 is provided with pins 134 on opposite sides thereof. Each pin 134 is rotatably received within a respective orifice 130 to create a hinge which allows upper support arm 132 to move (e.g. pivot) relative to lower support arms 128A, 128B. In addition, the top end of each upper support arm 128A, 128B is provided with an extension member 136A, 136B having a loop 138 provide therein. Each loop 138 is structured to receive a respective upper headgear strap 140 of the headgear component. In the illustrated embodiment, the terminal end of each extension member 136A, 136B having loop 138 provided therein is located below support frame 120 of forehead support 118. Alternatively, the terminal end of each extension member 136A, 136B having loop 138 provided therein may be located in line with or above support frame 120 of forehead support 118.

Patient interface device 102 as just described provides a mechanism for selectively (and finely) adjusting the force applied to the bridge of the nose of a patient by apex portion 105 of cushion 106 of mask 104 by varying the force applied by upper headgear straps 140. As noted elsewhere herein, the ability to provide subtle adjustments helps to minimize leaks and provide comfort to the patient. More specifically, as upper headgear straps 140 are tightened, the force applied by upper headgear straps 140 causes lower support arms 128A and 128B and extension members 136A and 136B to move (e.g., pivot) toward a sealing plane defined by sealing surface 107 of cushion 106. In addition, when patient interface device 100 is worn by a patient, such movement will cause lower support arms 128A and 128B and extension members 136A and 136B to move toward the face of the patient (with forehead support 118 being a fixed point of contact). As this happens, the hinge of hinge assembly 124 is allowed to rotate and close. As the hinge of hinge assembly 124 actuates by opening and closing, the nose bride force applied by apex portion 105 of cushion 106 of mask 104 is varied as the top of mask 104 will be caused to move relative to the patient's face (toward or away from the sealing plane described above). The bottom of mask 104 is secured in place by the force applied by lower headgear straps 116.

Figure 12:
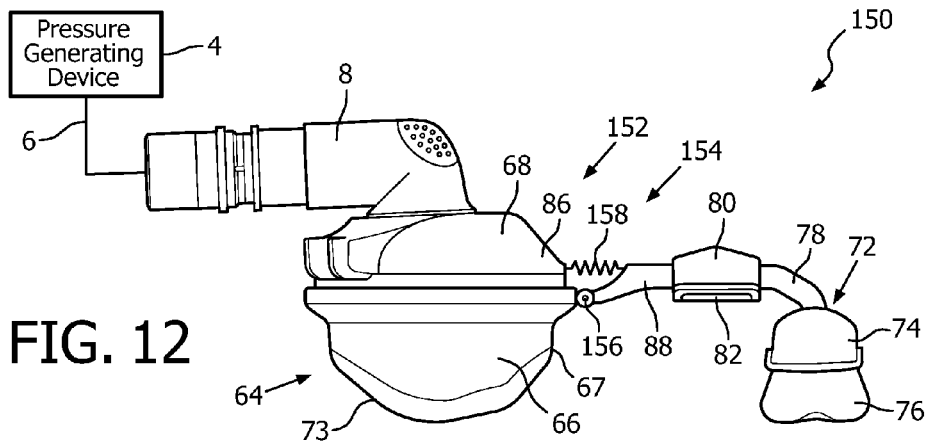
FIGS. 12-14 are side views of systems for providing a regimen of respiratory therapy to a patient according to still further alternative embodiments that employ still further alternative patient interface devices.

FIG. 12 is a side schematic view of system 150 adapted to provide a regimen of respiratory therapy to a patient according to still a further alternative exemplary embodiment of the invention. System 150 is similar to system 60, and like components are labeled with like reference numerals. System 150, however, includes an alternative patient interface device 152 having alternative hinge assembly 154. Alternative hinge assembly 154 includes hinge element 156, which may include a rotatable pin and orifice structure as described in connection with FIGS. 1-4, or a living hinge as described in connection with FIGS. 9 and 10. Alternative hinge assembly 154 also includes spring element 158, which in the illustrated embodiment is a metal spring.

Figure 13:
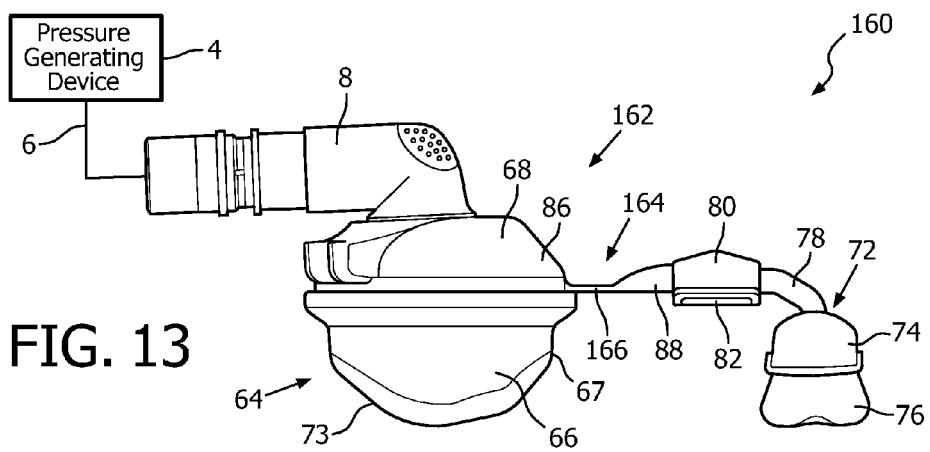

FIG. 13 is a side schematic view of system 160 adapted to provide a regimen of respiratory therapy to a patient according to still a further alternative exemplary embodiment of the invention. System 160 is similar to system 60, and like components are labeled with like reference numerals. System 160, however, includes an alternative patient interface device 162 having alternative hinge assembly 164. Alternative hinge assembly 164 comprises a thinned section 166, which in the exemplary embodiment is made of the same material as shell 68 and arm 88. The thickness of thinned section 166 allows is to flex and bend to a larger extent than shell 68 and arm 88.

Figure 14:
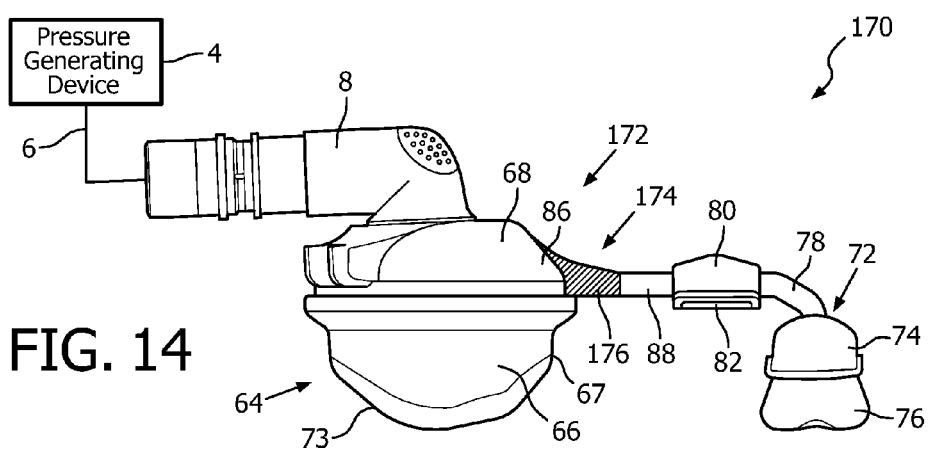

FIG. 14 is a side schematic view of system 170 adapted to provide a regimen of respiratory therapy to a patient according to still a further alternative exemplary embodiment of the invention. System 170 is similar to system 60, and like components are labeled with like reference numerals. System 170, however, includes an alternative patient interface device 172 having alternative hinge assembly 174. Alternative hinge assembly 174 comprises elastomer member 176 that is provided between top 86 of shell 68 and the bottom of arm 88. Elastomer member 176 may be made of a material such as silicone, rubber, polychloroprene or another suitable elastomer material.

As in the other embodiments describe herein, the actuation of alternative hinge assemblies 154, 164 and 174 provide for the selective control and adjustment of nose bridge pressure applied by apex portion 67 of cushion 66 of mask 64 in the respective embodiments. In addition, alternative hinge assemblies 154, 164 and 174 provide for a self aligning capability as described elsewhere herein (FIGS. 7 and 8).

While a number of different exemplary hinge assembly embodiments have been described in detail herein, it should be understood that other embodiments are also possible within the scope of the present invention. Thus, as used herein, the term "hinge assembly" shall mean any flexible coupling that joins two components in a manner that allows the two components to move relative to one another, such as in a rotating or pivoting manner.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device, comprising:
 a patient sealing assembly for delivering a flow of breathing gas to an airway of a patient, the patient sealing assembly including a cushion having a longitudinal axis defining a centerline passing through the cushion;
 a forehead support coupled to the patient sealing assembly, the forehead support being structured to engage a forehead of the patient when the patient interface device is donned by the patient, the forehead support having a support frame and a forehead cushion coupled to the support frame;
 a hinge assembly provided between a top portion of the patient sealing assembly and the forehead support;
 a strap frame structured to be coupled to a plurality of upper headgear straps, wherein the strap frame is positioned between the hinge assembly and an end portion of the forehead support; and
 an arm member, wherein the support frame of the forehead support is directly attached to a first end of the arm member at an attachment point, wherein a second end of the arm member opposite the first end is coupled to the strap frame, wherein the attachment point is positioned above a top side of the strap frame in a first direction that is normal to the centerline of the cushion such that the attachment point is spaced from the top side of the strap frame in the first direction.

2. The patient interface device according to claim 1, wherein the patient sealing assembly comprises a mask.

3. The patient interface device according to claim 2, wherein the mask has a rigid shell coupled to the cushion.

4. The patient interface device according to claim 3, wherein the forehead support is coupled to the shell and the hinge assembly is provided between a top portion of the shell and the forehead support.

5. The patient interface device according to claim 2, wherein the mask is a nasal mask, a nasal/oral mask, a nasal cannula, or a full face mask.

6. The patient interface device according to claim 1, wherein the cushion has a sealing surface structured to engage a face of a patient when the patient interface device is donned by the patient, wherein when the hinge assembly is in a first position, the sealing surface generally defines a sealing plane such that the centerline passing through the cushion is generally normal to the sealing plane, and wherein the hinge assembly is movable to a second position while engaged on a face of a patient such that a top portion of the cushion is caused to move toward the sealing plane.

7. The patient interface device according to claim 6, wherein the hinge assembly includes a support arm having a distal end directly or indirectly coupled to the forehead support, and wherein when the hinge assembly is moved to the second position the support arm moves toward the sealing plane.

8. The patient interface device according to claim 7, wherein the hinge assembly is structured to move in response to strapping forces being applied by the upper headgear straps when the patient interface device is donned by a patient.

9. The patient interface device according to claim 8, wherein the hinge assembly includes a living hinge.

10. The patient interface device according to claim 9, wherein the hinge assembly further includes at least one elastomer member provided adjacent to the living hinge.

11. The patient interface device according to claim 8, wherein the hinge assembly includes a spring element provided between the patient sealing assembly and the support arm.

12. The patient interface device according to claim 8, wherein the hinge assembly includes an elastomer member provided between the patient sealing assembly and the support arm.

13. The patient interface device according to claim 7, wherein the hinge assembly includes second and third support arms extending upwardly from the patient sealing assembly, and wherein the support arm is moveably received and held between the second and third support arms.

14. The patient interface device according to claim 13, wherein the second and third support arms have an extension member coupled thereto, and wherein the extension members form the strap frame.

15. The patient interface device according to claim 14, wherein the distal end of each extension member is located between the forehead support and the patient sealing assembly.

* * * * *